United States Patent
Maher et al.

[11] Patent Number: 5,707,218
[45] Date of Patent: Jan. 13, 1998

[54] IMPLANTABLE ELECTRIC AXIAL-FLOW BLOOD PUMP WITH BLOOD COOLED BEARING

[75] Inventors: Timothy R. Maher, Orangevale; Lynn P. Taylor, Camino; Pieter W. J. C. le Blanc, Pollock Pines; Kenneth C. Butler, Carmichael, all of Calif.

[73] Assignee: Nimbus, Inc., Rancho Cordova, Calif.

[21] Appl. No.: 710,211

[22] Filed: Sep. 13, 1996

Related U.S. Application Data

[63] Continuation-in-part of Ser. No. 424,165, Apr. 19, 1995, Pat. No. 5,588,812.
[51] Int. Cl.$^6$ ............................................. F04B 17/03
[52] U.S. Cl. ............................ 417/356; 415/900; 604/151
[58] Field of Search .............................. 417/356, 355, 417/365, 423.1, 423.12, 423.15; 415/900; 604/151; 600/16; 623/3

[56] References Cited

U.S. PATENT DOCUMENTS

| | | | |
|---|---|---|---|
| 3,433,163 | 3/1969 | Sheets et al. | 417/356 |
| 4,625,712 | 12/1986 | Wampler | 128/1 D |
| 4,704,712 | 11/1987 | Siryj | 369/249 |
| 4,994,078 | 2/1991 | Jarvik | 623/3 |
| 5,112,200 | 5/1992 | Isaacson et al. | 415/900 |
| 5,158,440 | 10/1992 | Cooper et al. | 417/355 |
| 5,211,546 | 5/1993 | Isaacson et al. | 415/900 |
| 5,399,074 | 3/1995 | Nose et al. | 417/423.12 |
| 5,507,629 | 4/1996 | Jarvik | 415/900 |
| 5,527,159 | 6/1996 | Bozeman, Jr. et al. | 415/900 |

*Primary Examiner*—Timothy Thorpe
*Assistant Examiner*—Peter G. Korytnyk
*Attorney, Agent, or Firm*—Harry G. Weissenberger

[57] ABSTRACT

An axial-flow blood pump has a rotor suspended in ball-and-cup bearings which are blood-cooled but not actively blood-lubricated. The ball-and-cup structures are made of highly heat-conductive material and are in heat-transferring contact with heat-conductive stator blades that serve as heat sinks for the bearings. The ball-and-cup structures are radially much smaller than the stator blades. The ball-and-cup interface has so small a gap that the ball-to-cup structures present an essentially continuous surface to the blood flow.

15 Claims, 6 Drawing Sheets

IMPLANTABLE ELECTRIC AXIAL-FLOW BLOOD PUMP WITH BLOOD COOLED BEARING

This case is a continuation-in-part of application Ser. No. 08/424,165 filed Apr. 19, 1995, now U.S. Pat. No. 5,588,812.

FIELD OF THE INVENTION

This invention relates to implantable axial-flow blood pumps using blood-immersed rotors with a non-thrombogenic suspension, and more particularly to a pump configuration using a blood-cooled self-aligning ball-and-cup rotor support which does not use blood as a bearing fluid.

BACKGROUND OF THE INVENTION

Conventional axial-flow blood pumps with hydrodynamic bearings used in cardiac assist, such as the pump disclosed in U.S. Pat. No. 4,625,712, required a supply of purge fluid to prevent blood from entering their hydrodynamic journal and thrust bearings and causing thrombus formation, hemolysis and bearing seizure. Because of this need for an external fluid supply, that type of pump is not well suited for long-term implants.

Ideally, implantable blood pumps should require no bearing fluid or else use the pumped blood itself, or components of the pumped blood, as a bearing fluid. Indeed, constructions which allow this have been proposed, among others, by R. K. Jarvik in U.S. Pat. No. 4,994,078 and by Isaacson et al. in U.S. Pat. No. 5,112,200. The problem with these constructions is that they rely on cylindrical radial or journal bearings which mechanically support the rotor against radial movement. In typical embodiments of the prior art, those bearings are interior film bearings, i.e. blood-lubricated cylindrical hydrodynamic bearings through which blood serum is drawn by the pressure differential between the ends of the cylinder. In order to prevent blood cells from entering the bearing and being hemolyized, the bearing clearance is made so small that blood cells are essentially precluded from entering the bearing.

Alternatively, as taught by U.S. Pat. No. 4,704,121 to Moise, bearing fluid for a magnetically driven blood pump can be obtained by filtering a portion of the pumped blood through a filter which retains the blood cells and proteins but passes the serum.

Papers entitled "Axial Flow Ventricular Assist Device: System Performance Considerations" (*Artificial Organs*, Vol. 18, No. 1 pp., 44–48 (1994) and "An Ultimate, Compact, Seal-less Centrifugal Ventricular Assist Device: Baylor C-Gyro Pump" (*Artificial Organs*, Vol. 18, No. 1 pp. 17–24 (1994) describe, respectively, an axial-flow blood pump and a centrifugal blood pump using blood-lubricated pivot bearings.

The journal or radial bearing concepts of the prior art have a potential flaw which puts them at risk to bearing seizure, and/or ultimately causes them to undergo excessive bearing material wear. Fundamentally, this is due to the length of the bearing, the diminished heat removal capacity caused by the location of the bearings inside the rotor or stator, and to the lack of significant bearing through-flow in the interior film designs. The comparatively long and extremely narrow gaps the blood must pass through are subject to be plugged by denatured blood products. This is particularly true in those prior art embodiments in which the journal bearing is closed at one end, so that blood cannot flow through it. Even in those designs in which the motor has sufficient torque to machine through any residue formed, significant material wear can occur over the long term and reduce the pump's useful life. Also, in journal bearings using the extremely small tolerances necessary to prevent entry of blood cells, the slightest misalignment of the rotor with respect to the stator can seriously impair the functioning and the life of the pump. Finally, the performance and longevity of journal bearings, including interior film blood bearings, are significantly more dependent on difficult-to-control patient variables such as blood chemistry and hemorrhology than arrangements which do not use blood lubrication.

A need therefore exists for an implantable blood pump in which active blood lubrication is unnecessary, alignment is auto-adjusting, the interface area between rotating and stationary elements is kept very small, and the interface has superior heat-removing ability and resists any shape changes due to wear.

SUMMARY OF THE INVENTION

Copending application Ser. No. 08/424,165 solves the above problems of the prior art by providing a pump rotor with a ball-and-cup support that has very small mating surfaces with no significant gap between them. The ball-and-cup support is a dry bearing composed of very hard materials with a low coefficient of friction and a high heat conductivity. It does not require (and in fact seeks to avoid) the introduction of a lubricating blood serum film between the mating surfaces. The support is washed externally by the free-flowing pumped blood stream to remove the frictional heat generated at the rotary-stationary interface. The high-heat conductivity of the ball-and-socket assembly materials, as well as the relatively small size of the ball-and-cup assembly, allow an efficient heat transfer between the bearing and the blood stream. In accordance with an aspect of the present application, this heat transfer is enhanced by using the inlet stator blades of the pump as cooling fins for the ball-and-cup bearing.

The hardness of the bearing materials—preferably, as disclosed herein, a diamond film backed by silicon carbide—maintains throughout the useful life of the pump extremely close tolerances necessary to keep blood serum out of the bearing. Silicon carbide is preferred for this application because it has high temperature conductivity and therefore allows the bearing to run cooler when washed by the blood stream. In addition, any wear that occurs in spite of the hardness of the ball and cup materials is compensated by so shaping the balls and cups that the shapes of the hemispherical surfaces with respect to each other are not changed by wear, and by optionally maintaining a preload, regardless of wear, with the aid of a resilient biasing member.

In accordance with another aspect of the invention, the pump rotor is formed with a tail cone which is nested inside the stator blades at the outlet end of the pump. This construction has the double advantage of substantially shortening the overall length of the pump to reduce its priming volume, and of washing the outlet and ball-and-cup structure with a blood stream that still has a substantial circumferential velocity component for improved heat removal action.

DESCRIPTION OF THE PREFERRED EMBODIMENTS

Figure 1:
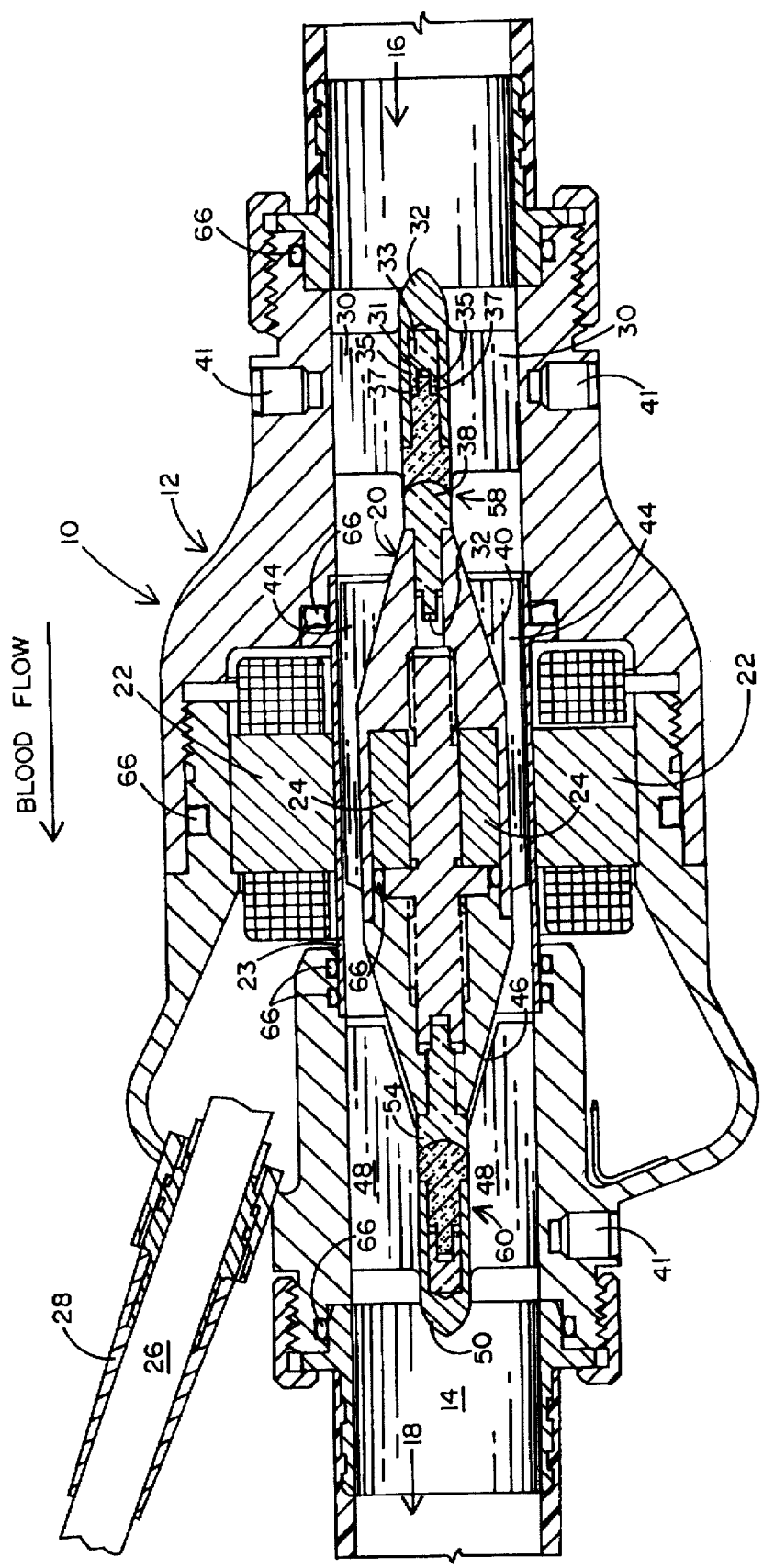
FIG. 1 is a longitudinal section of one embodiment of the pump of this invention.
Figure 2:
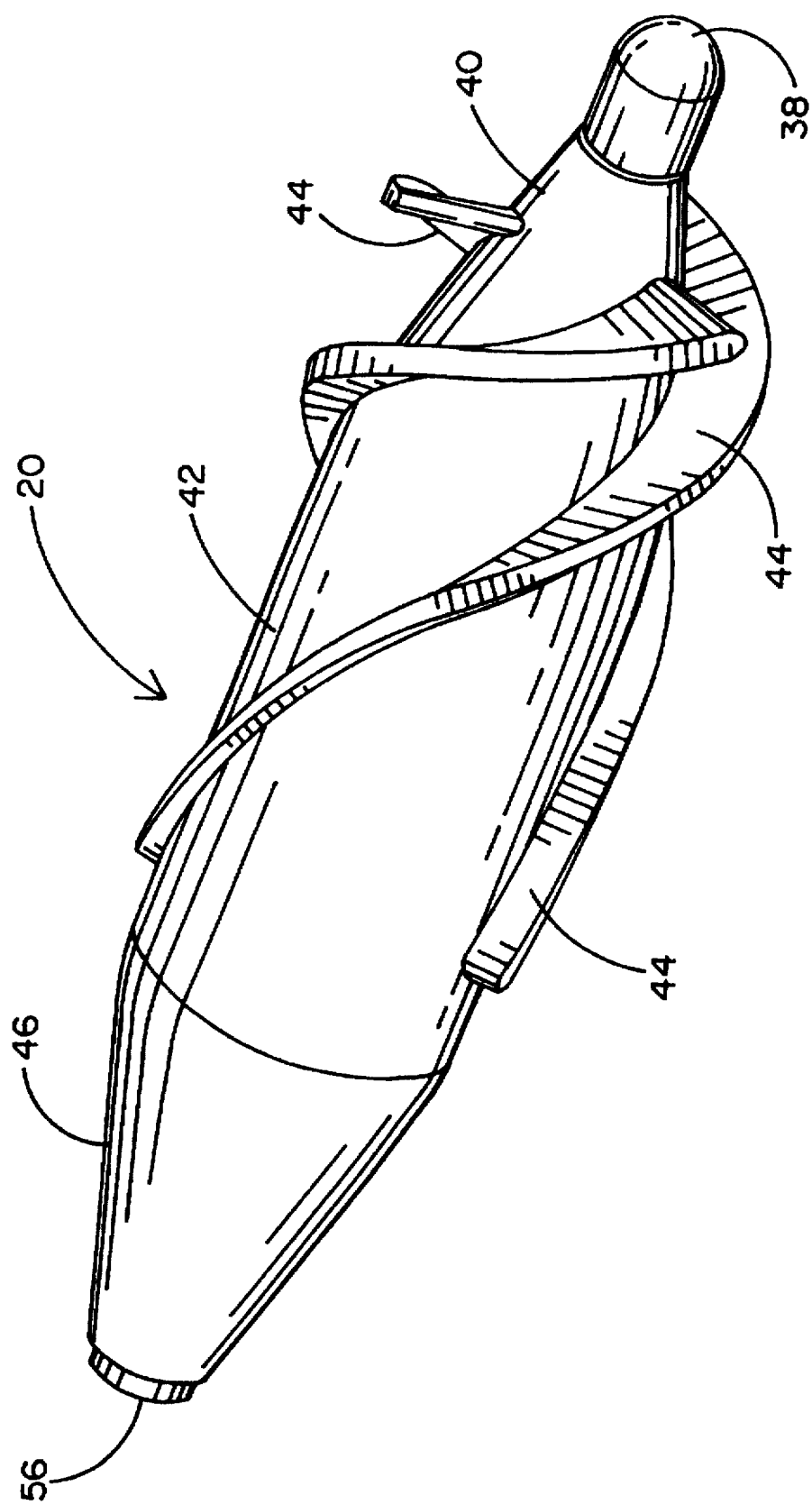
FIG. 2 is a perspective view of the pump rotor of the pump of FIG. 1.
Figure 3:
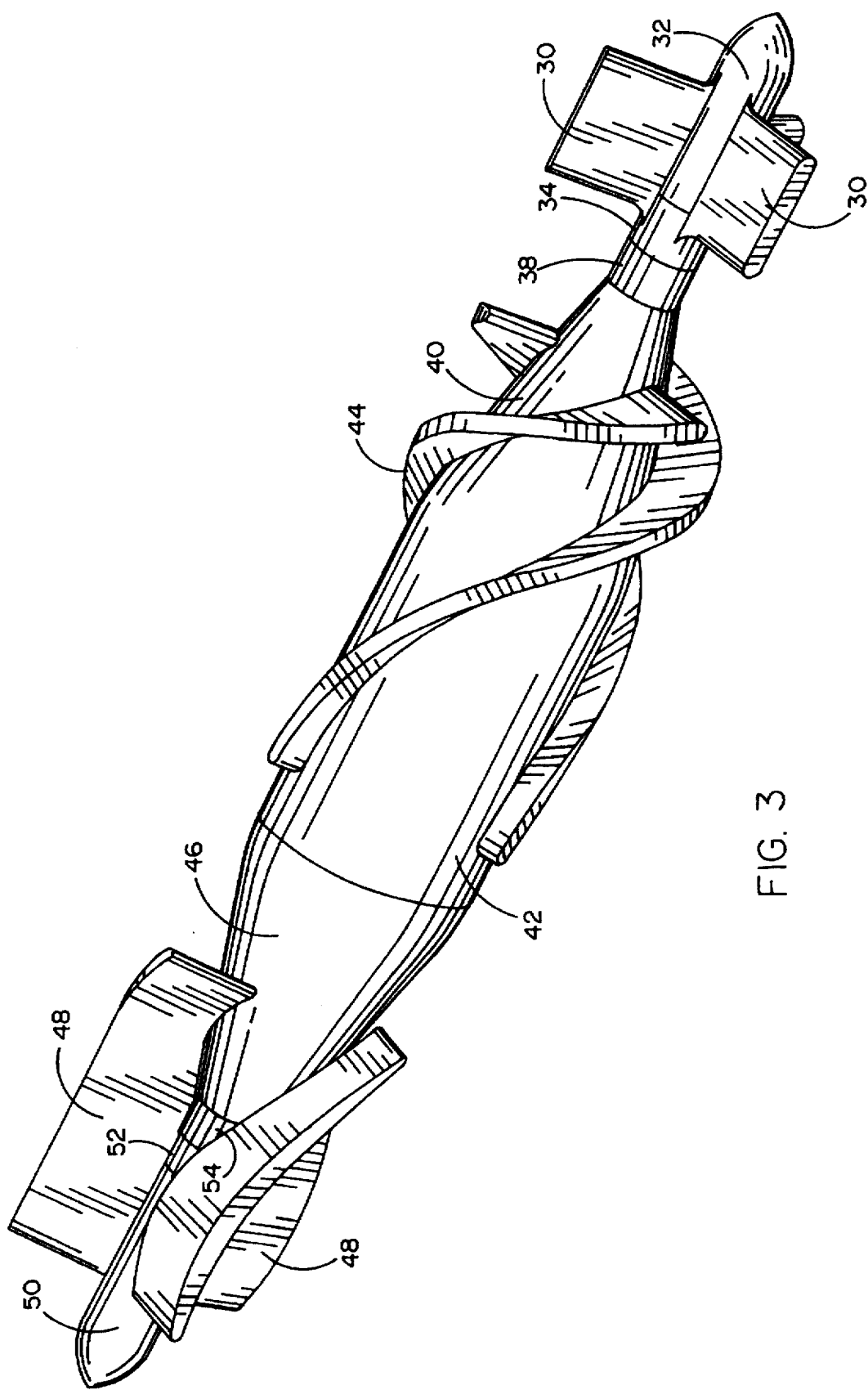
FIG. 3 is a perspective view of the pump rotor and stator assemblies of FIG. 1 with the housing and motor stator removed.
Figure 4:
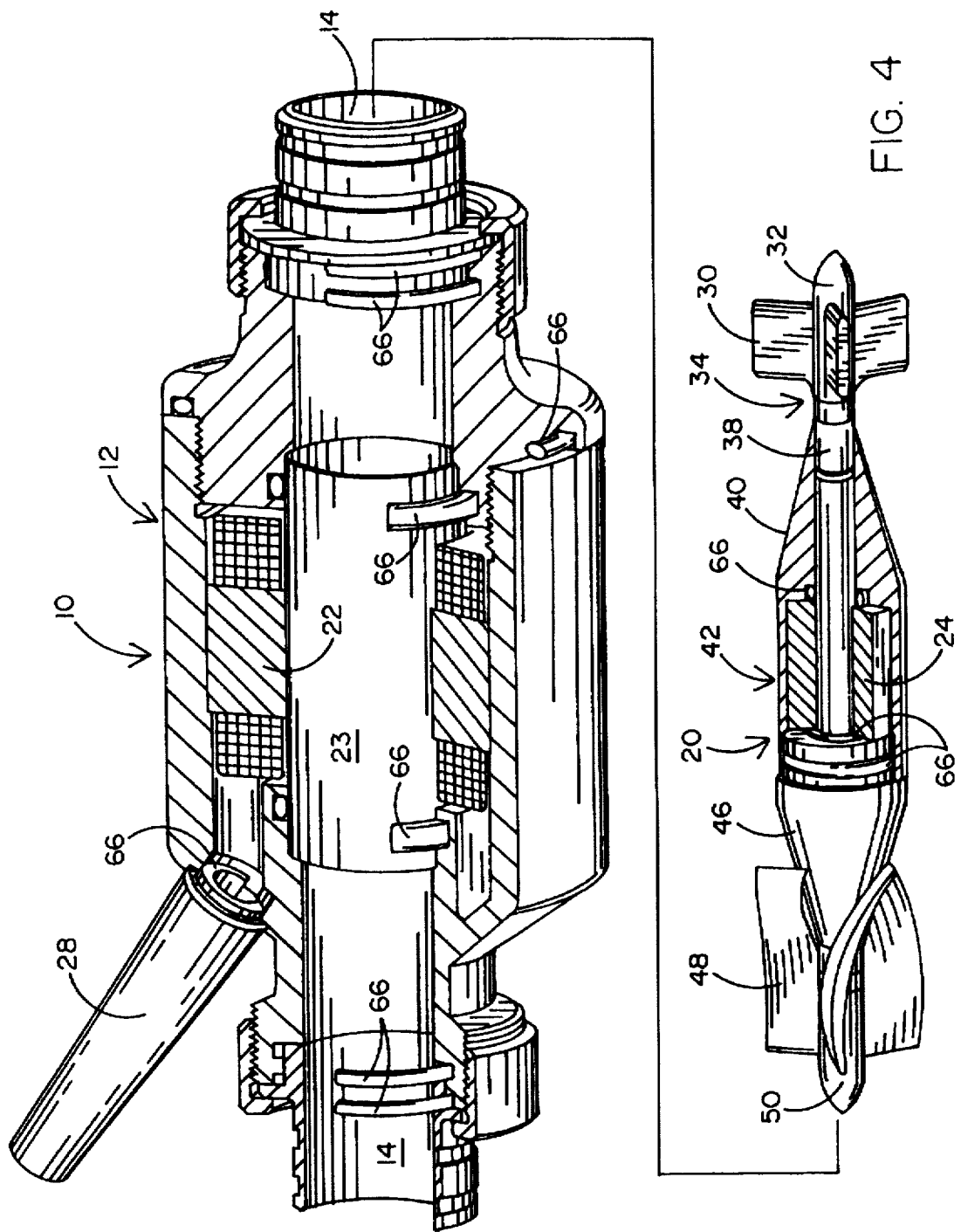
FIG. 4 is a cutaway exploded view of the pump of FIG. 1.

FIG. 1 shows an axial cross section of one embodiment of the inventive pump 10. The pump housing 12 defines a cylindrical blood conduit 14 through which blood is pumped from the inlet 16 to the outlet 18 by the pump rotor 20 best shown in FIG. 2. Motive power for the pump rotor 20 is provided by the interaction of a motor stator 22 surrounding the stator tube 23 in the housing 12, and a motor rotor 24 fixedly mounted in the pump rotor 20 around shaft 25. Electrical power is supplied to the motor stator 22 by a cable 26 extending through the wiring conduit 28.

Inside the blood conduit 14, straight inlet stator blades 30 made of a highly heat-conductive material support an inlet hub 32, also made of a highly heat-conductive material, which contains the cup member 34. The cup member 34, which is constructed of a hard and also highly heat-conductive material such as silicon carbide, fits tightly into the hub 32. A key assembly 33 fixed in hub 32 provides a thermal expansion space 31 for the cup member 34, and also provides keys 35 which engage slots 37 of the cup member 34 to hold the cup member 34 against rotation.

In accordance with the present invention, the stator blades 30 extend from near the inlet end of hub 32 all the way to the downstream end of cup member 34, i.e. all the way to the interface between ball 38 and cup 34. By tightly fitting the cup member 34 into the blades 30, and the ball member 38 into the nose cone 40 in heat-transferring engagement, the blades 30 act as heat sinks not only along the hub 32, but directly at the rotary/stationary interface between cup 34 and ball 38 where the frictional heat of the bearing is generated. Likewise, the nose cone 40 provides a heat sink for the ball member 38. Considering that the radial extent of the blades 30 is considerably larger than the diameter of cup member 34, the blades 30 can dissipate a substantial amount of frictional heat. The stator blades 30 are held in place in the blood conduit 14 by setscrews 41 which, when tightened, deform the housing 12 sufficiently to wedge the blades 30 firmly in the blood conduit 14.

In order to reduce the generation of heat in the first place, the interengaging surfaces of the ball 38 (which is keyed to nose cone 40) and cup 34 are preferably coated with a thin (ca. 1.0μ) layer of highly wear-resistant diamond film. This material has a relatively low coefficient of friction, as compared to other hard bearing materials, and is therefore particularly suited to the present application in which frictional heat is a significant parameter to be minimized.

The nose cone 40 and the body 42 of pump rotor 20 support the rotor blades 44 which accelerate the blood flowing through blood conduit 14 and impart a circumferential spin to the blood flow. In accordance with this invention, the tail cone 46 of pump rotor 20 is nested within the outlet stator blades 48. The outlet stator blades 48 slow and de-spin the blood flow for discharge into the outlet 18. The outlet stator blades 48 also support the outlet hub 50 into which the outlet ball 52 is tightly fit and keyed. The ball 52 cooperates with an outlet cup 54 tightly fit and keyed into the tail cone 46.

The nesting of the rotor tail cone 46 in the outlet stator blades 48 has several advantages: for one, it shortens the pump 10 substantially, so that its priming volume (a significant factor in surgical procedures) is materially reduced; and for another, it allows improved cooling of the outlet ball-and-socket assembly 52, 54. This is so because at the location of the ball-and-socket assembly in about the longitudinal center of the outlet stator blades 48, the cooling blood stream still has a rotational flow component in addition to its axial flow component. Also, as described above in connection with stator blades 30, a press fit of the ball member 52 into the blades 48, and of the cup member 54 into the tail cone 46, allows the blades 48 and tail cone 46 to function as large heat sinks for the rotary/stationary interface of ball 52 and cup 54.

The two halves 62, 64 of the pump rotor 20 are held together by screwing them onto the shaft 25.

It will be noted that except for the actual ball or cup surface, the ball member 38 and the cup member 34 are identical. Consequently, if desired, they can be reversed from their relative positions in FIG. 1 if doing so should become desirable.

The provision of a thermal expansion space 31 behind both the cup member 34 and the ball member 38 makes it possible to absorb any thermal expansion of those members in the hub 32 and rotor 20, respectively. It is thus possible to maintain extremely close tolerances between the interengaging surfaces of the cup member 34 and the ball member 38 over a wide range of bearing temperatures.

The correct mating or preloading of cup member 34 and ball member 38 (and, at the other end of the rotor 20, the cup member 54 and ball member 52) without any biasing force is accomplished during assembly by an extremely precise positioning of the hub 32 and stator blades 30 before tightening the setscrews 41 which lock the hub-and-stator subassembly in place. The resulting factory-set preload is maintained during the life of the pump 10 due to the hardness of the diamond film with which the interengaging ball and cup surfaces are coated.

Figure 5:
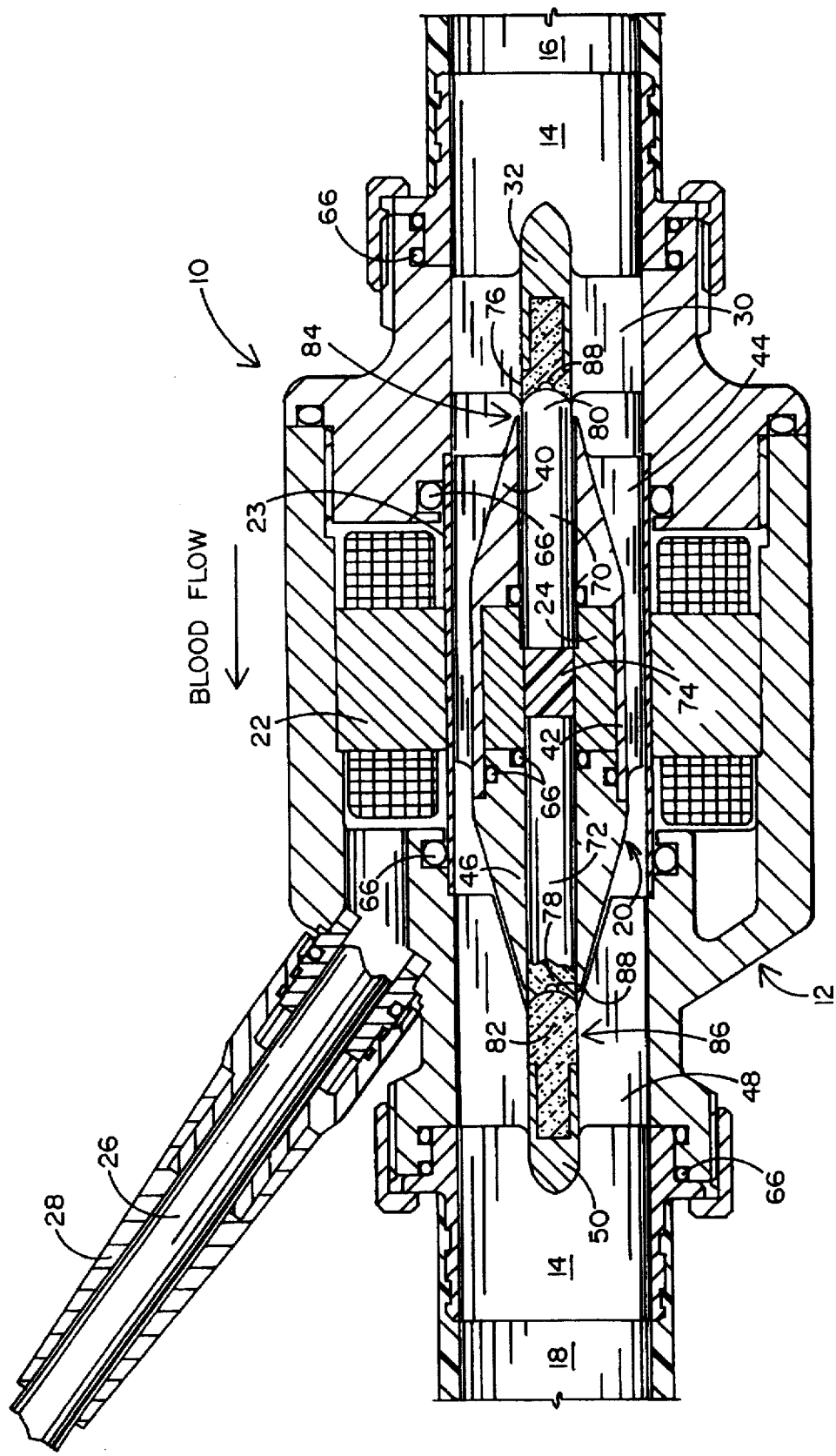
FIG. 5 is a longitudinal section of another embodiment of the pump of the invention.
Figure 6:
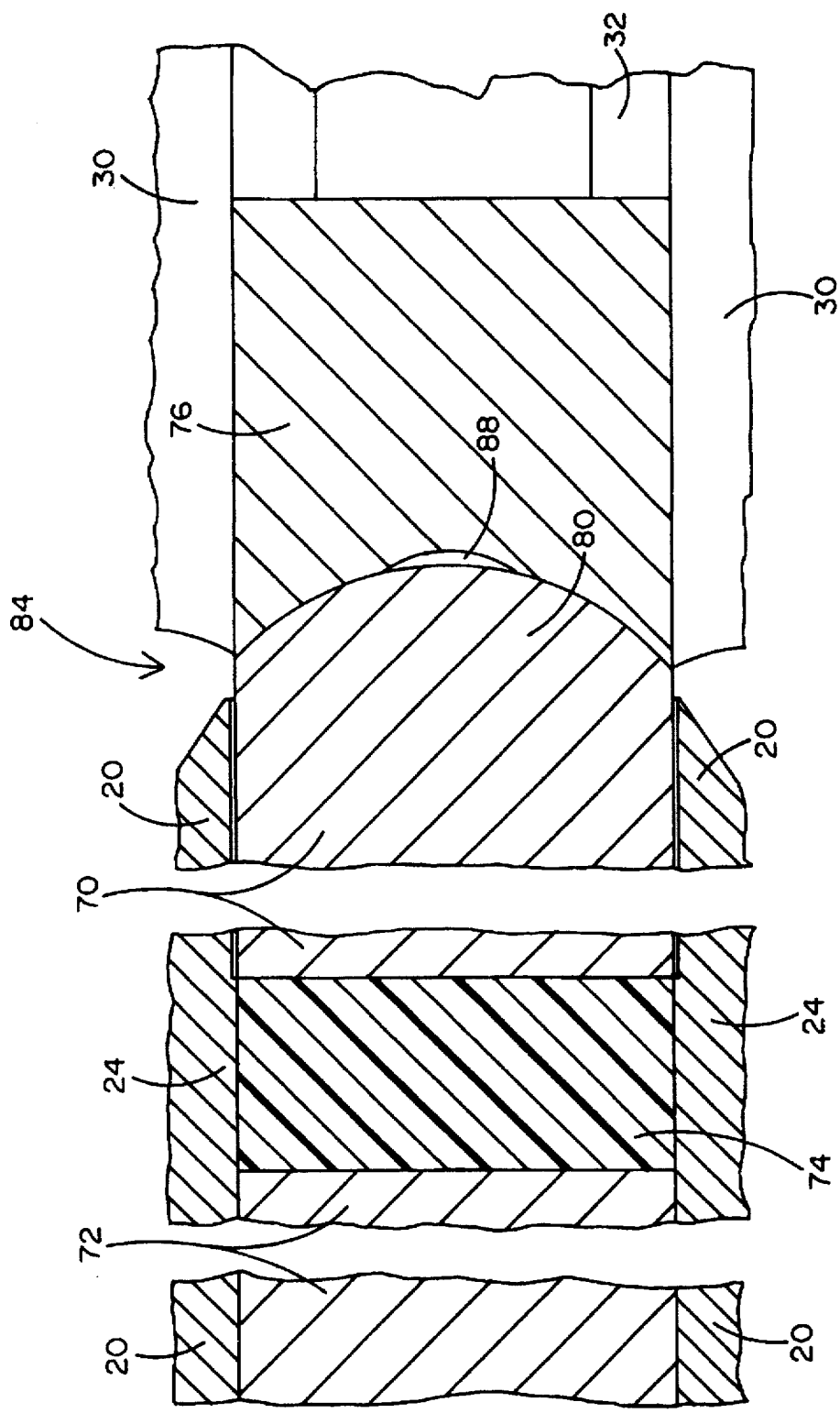
FIG. 6 is a detailed partial section of the rotor and stator of the pump of FIG. 5.

In accordance with an alternative embodiment of the invention illustrated in FIGS. 5 and 6, the pump rotor 20 is provided with a shaft assembly composed of a fixed shaft portion 72, a shaft portion 70 which is axially slidable within the rotor 20 but non-rotatable with respect thereto, and a resilient plug 74 between them. The shaft portion 70 is fitted into rotor 20 with a small enough tolerance (e.g. 50μ) to prevent any blood or serum entering the rotor 20, although it would not matter if it did, because shaft portion 70 does not rotate with respect to rotor 20. The slidable portion 70 is preferably at the outlet end of the rotor 20, as the thrust forces acting on it are less at that end.

In accordance with the invention, the balls 80, 82 and the respective cups 76, 78 are lapped together during manufacture so that the radii of their hemispherical mating surfaces are as identical as manufacturing techniques can make them. As a result, the gap between the mating surfaces of the balls and their respective cups is extremely small—on the order of 0.25–0.5μ—when the balls and cups are biased against each other by the plug 74.

When the pump of this invention is new, a microscopic amount of lubricant applied during assembly fills this extremely narrow gap. As the pump wears, a small amount of blood serum may penetrate into the gap, but during the useful life of the pump, not enough serum leakage would occur to affect the interaction of the mating surfaces.

The hemispherical surfaces of the balls 80, 82 and the cups 76, 78 are preferably less than half hemispheres; for example, the radius of the ball or cup may be about 2 mm, and the diameter of the shaft portion 70 or 72 may be about 3 mm. This improves the sturdiness of the cup rim and results in more uniform wear. Also, this allows the diameter of the cup member 34 and ball member 38 at their interface to be identical, so that the blood stream sees an axially continuous surface at the interface which allows a smooth, undisturbed blood flow across the interface. A recess 88 may be formed in the center of the cup 76 or 78 to facilitate manufacturing and provide a reservoir for receiving the manufacturing lubricant.

It will be apparent from an examination of FIG. 6 that a slight angular misalignment of the axes of the ball and the cup will not affect the operation of the ball-and-cup structure, as the mating surface of the ball and cup mate in exactly the same way regardless of any slight axial angle alignment variation.

During assembly of the embodiment of FIGS. 5 and 6, the shaft portions 70, 72 are pressed together with sufficient force to deform the resilient plug 74. As the cups 76, 78 wear or the balls and cups expand due to frictional heat, the plug 74 expands and contracts as necessary to maintain an even pressure of the balls 80, 82 against the cups 76, 78. Optionally, preloading may be achieved, if desired, by spring-loading cup member 34 and ball member 52 with springs (not shown) so that the cup 34 and ball 52 can follow any longitudinal movement of pump rotor 20. In order to give the ball-and-cup structures a sufficient useful life (up to five years' reliability is expected of long-term implants of this type) in spite of the small interface surface, the shaft portion 70 in the embodiment of FIG. 5 is made of alumina. The shaft portion 72 is preferably made of synthetic ruby, while the cup 78 is made of silicon-carbide-whisker-reinforced alumina. It will be understood that although these materials are preferred, other materials that are hard, wear-resistant, machinable and biocompatible, and which have a relatively high thermal conductivity and relatively low friction coefficient, can be substituted therefor. These very hard substances (as for example the diamond film coating discussed above) make it possible to reduce the already low wear of the inventive ball-and-cup structures to a point where the longevity requirement can be met or exceeded. At the same time, the superior thermal conductivity of silicon carbide and synthetic ruby helps to prevent heat build-up which might promote thrombus formation.

The advantage of the inventive ball-and-cup bearing is that the structures 58, 60 and 84, 86 are highly washed and efficiently cooled external bearings, i.e. bearings in which no blood flows into or through any channel located inside the pump rotor or stator. The bearing surface is very small; there is no unidirectional blood flow through the bearing and therefore no accumulation of blood cells (which may be too large to pass through the bearings) around the bearing interface, nor any thrombus formation at the interface; and the perimeter of the bearing surface is continuously washed by a smooth-flowing non-turbulent main blood stream. In addition, the outlet ball-and-cup structure 60 or 86 is even more efficiently washed because, as printed out above, at the location of that structure less than half way along the stator blades 48, the blood stream still has considerable circumferential velocity.

All parts of the pump not intended to be washed by the blood stream are sealed off from it by O-rings generally shown as 66.

It is understood that the exemplary implantable electric axial-flow blood pump described herein and shown in the drawings represents only a presently preferred embodiment of the invention. Indeed, various modifications and additions may be made to such embodiment without departing from the spirit and scope of the invention. Thus, other modifications and additions may be obvious to those skilled in the art and may be implemented to adapt the present invention for use in a variety of different applications.

We claim:

1. An implantable blood pump, comprising:
   a) a cylindrical blood conduit;
   b) a motor stator surrounding said blood conduit;
   c) a pump rotor having inlet and outlet ends and containing a motor rotor for motive interaction with said motor stator, said pump rotor being arranged to rotate in said blood conduit;
   d) inlet stator blades disposed in said blood conduit, said inlet stator blades supporting an inlet hub;
   e) outlet stator blades disposed in said blood conduit, said outlet stator blades supporting an outlet hub; and
   f) a non-hydrostatic ball-and-cup bearing structure interposed between each of said inlet and outlet ends of said pump rotor and the corresponding one of said hubs for supporting said rotor, said ball-and-cup structure forming ball-to-cup interfaces having a small enough gap to substantially prevent blood serum from entering into said interface, and said ball-and-cup structure being washed by the blood flow through said blood conduit;
   g) said stator blades at each end of said pump rotor being in heat-transferring contact with the corresponding one of said ball-and-cup structures, said ball-and-cup structures having an outside diameter substantially smaller than the radial extent of said stator blades between said hubs and said blood conduit.

2. The blood pump of claim 1, in which said ball-and-cup structures present a sufficiently continuous surface across said interface to allow blood flow across the perimeter of said interface without discontinuity.

3. The blood pump of claim 1, in which said ball-and-cup structures, hubs, and stator blades are all formed from highly heat-conductive material, and are in heat-transferring contact with one another.

4. The blood pump of claim 1, in which said interfaces are formed of a hard material with a low friction coefficient.

5. The blood pump of claim 1, in which said ball-and-cup structures are formed of silicon carbide coated at said interface with a diamond film.

6. The blood pump of claim 1, in which the mating surfaces of the balls and cups of said ball-and-cup structures are of essentially identical radius.

7. The blood pump of claim 6, in which said balls and cups are biased against one another with sufficient force to substantially prevent penetration of blood between said mating surfaces.

8. An implantable blood pump, comprising:
   a) a cylindrical blood conduit;
   b) a motor stator surrounding said blood conduit;
   c) a pump rotor having inlet and outlet ends and containing a motor rotor for motive interaction with said motor stator, said pump rotor being arranged to rotate in said blood conduit;
   d) inlet stator blades disposed in said blood conduit, said inlet stator blades supporting an inlet hub;
   e) outlet stator blades disposed in said blood conduit, said outlet stator blades supporting an outlet hub; and
   f) a ball-and-cup structure interposed between each of said inlet and outlet ends of said pump rotor and the corresponding one of said hubs for supporting said rotor, said ball-and-cup structure being washed by the blood flow through said blood conduit;

g) said stator blades at each end of said pump rotor being in heat-transferring contact with the corresponding one of said ball-and-cup structures, said ball-and-cup structures having an outside diameter substantially smaller than the radial extent of said stator blades between said hubs and said blood conduit;

h) said inlet and outlet hubs being axially fixed with respect to said motor stator, said motor rotor having a shaft including a pair of shaft portions axially movable with respect to each other but non-rotatable with respect to said rotor, and a resilient element interposed between said shaft portions and arranged to bias said shaft portions axially away from each other.

9. The blood pump of claim 8, in which said resilient element is a plug.

10. The blood pump of claim 8, in which one of said shaft portions is axially fixed with respect to said rotor, and the other shaft portion is axially slidable with respect to said rotor.

11. The blood pump of claim 10, in which said slidable shaft portion is on the outlet side of said rotor.

12. The blood pump of claim 11, in which said slidable shaft portion has a ball on its inlet end and is made of synthetic ruby, and said fixed shaft portion has a cup on its end and is made of silicon-carbide-whisker-reinforced alumina.

13. The blood pump of claim 8, in which said ball-and-cup structures are composed of an element constructed of synthetic ruby facing an element constructed of silicon-carbide-whisker-reinforced alumina.

14. The blood pump of claim 13, in which said pump rotor has a longitudinal shaft, each end of which is an element of one of said ball-and-cup structures, said shaft being said element constructed of alumina.

15. An implantable blood pump, comprising:

a) a cylindrical blood conduit;

b) a motor stator surrounding said blood conduit;

c) a pump rotor having inlet and outlet ends and containing a motor rotor for motive interaction with said motor stator, said pump rotor being arranged to rotate in said blood conduit;

d) inlet stator blades disposed in said blood conduit, said inlet stator blades supporting an inlet hub;

e) outlet stator blades disposed in said blood conduit, said outlet stator blades supporting an outlet hub; and f) a ball-and-cup structure interposed between each of said inlet and outlet ends of said pump rotor and the corresponding one of said hubs for supporting said rotor, said ball-and-cup structure being washed by the blood flow through said blood conduit;

g) said stator blades at each end of said pump rotor being in heat-transferring contact with the corresponding one of said ball-and-cup structures, said ball-and-cup structures having an outside diameter substantially smaller than the radial extent of said stator blades between said hubs and said blood conduit;

h) said ball-and-cup structures being composed of hard wear-resistant, machinable biocompatible materials which have a high thermal conductivity.

* * * * *

UNITED STATES PATENT AND TRADEMARK OFFICE
CERTIFICATE OF CORRECTION

| | | |
|---|---|---|
| PATENT NO. | : 5,707,218 | Page 1 of 1 |
| APPLICATION NO. | : 08/710211 | |
| DATED | : January 13, 1998 | |
| INVENTOR(S) | : Maher et al. | |

It is certified that error appears in the above-identified patent and that said Letters Patent is hereby corrected as shown below:

At Column 1, immediately following the first full paragraph, please insert the following paragraph:

--STATEMENT AS TO FEDERALLY SPONSORED RESEARCH
Funding for the work described herein was provided in part by the National Institutes of Health, Grant No. NO1-HV-58155. The federal government may have certain rights in the invention.--

Signed and Sealed this

Twentieth Day of February, 2007

JON W. DUDAS
*Director of the United States Patent and Trademark Office*